(12) United States Patent
Perkins et al.

(10) Patent No.: US 8,343,233 B2
(45) Date of Patent: Jan. 1, 2013

(54) VALVE SYSTEM FOR PROSTHETICS

(76) Inventors: Matt Perkins, Boise, ID (US); Dale Perkins, Twin Falls, ID (US)

( * ) Notice: Subject to any disclaimer, the term of this patent is extended or adjusted under 35 U.S.C. 154(b) by 53 days.

(21) Appl. No.: 12/826,633

(22) Filed: Jun. 29, 2010

(65) Prior Publication Data

US 2011/0022182 A1    Jan. 27, 2011

Related U.S. Application Data

(63) Continuation-in-part of application No. 11/527,752, filed on Sep. 25, 2006, now abandoned.

(60) Provisional application No. 60/719,785, filed on Sep. 24, 2005.

(51) Int. Cl.
*A61F 2/80* (2006.01)

(52) U.S. Cl. ............................................ 623/34; 623/33

(58) Field of Classification Search ...................... 623/34
See application file for complete search history.

(56) References Cited

U.S. PATENT DOCUMENTS

| | | | |
|---|---|---|---|
| 1,586,015 A | 5/1926 | Underwood | |
| 2,530,285 A | 11/1950 | Catrains | |
| 2,533,404 A | 12/1950 | Sharp et al. | |
| 2,790,180 A | 4/1957 | Hauser | |
| 4,010,052 A | 3/1977 | Edwards | |
| 4,106,745 A | 8/1978 | Carrow | |
| 4,655,779 A | 4/1987 | Janowiak | |
| 5,007,937 A | 4/1991 | Fishman et al. | |
| 5,201,774 A | 4/1993 | Greene | |
| 5,490,537 A | 2/1996 | Hill | |
| 5,658,353 A | 8/1997 | Layton | |
| 5,709,017 A | 1/1998 | Hill | |
| 5,807,303 A | 9/1998 | Bays | |
| 6,287,345 B1 | 9/2001 | Slemker et al. | |
| 6,334,876 B1 | 1/2002 | Perkins | |
| 6,361,568 B1 | 3/2002 | Hoerner | |
| 6,508,842 B1 | 1/2003 | Caspers | |
| 6,544,292 B1 | 4/2003 | Laghi | |
| 6,626,952 B2 | 9/2003 | Janusson et al. | |
| 6,706,364 B2 | 3/2004 | Janusson et al. | |
| 6,761,742 B2 | 7/2004 | Caspers | |
| 6,797,008 B1 | 9/2004 | Arbogast et al. | |
| 7,448,407 B2 | 11/2008 | Alley et al. | |
| 2004/0181290 A1 | 9/2004 | Caspers | |
| 2004/0260403 A1 | 12/2004 | Patterson et al. | |
| 2007/0005149 A1* | 1/2007 | Egilsson et al. | 623/34 |
| 2007/0112440 A1 | 5/2007 | Perkins et al. | |
| 2009/0198346 A1 | 8/2009 | Perkins et al. | |
| 2010/0087931 A1* | 4/2010 | Bogue | 623/34 |

* cited by examiner

*Primary Examiner* — Bruce E Snow
*Assistant Examiner* — Melissa Hoban
(74) *Attorney, Agent, or Firm* — Pedersen and Company, PLLC; Ken J. Pedersen; Barbara S. Pedersen

(57) ABSTRACT

A valve system for a prosthetic hard socket includes an elastomeric valve member that rests in a closed position that seals against a valve housing surface, and opens at a low "crack" or "pop" pressure, for example, when the pressure inside the distal region of the socket well is 1-3 psi above the air pressure outside the hard socket. The elastomeric valve member exhibits a very accurate and reproducible response at the low crack pressure, and, in addition, sound dampening and/or filtration pads further reduce sound and fouling of the preferred elastomeric valve member. The valve may be installed without leaks even on highly-curved thin-walled sockets, as the broad base of the valve is adhesively attached to the outside of the socket, and optionally a rearward protrusion extends into a hole in the socket without protruding into the socket well.

1 Claim, 8 Drawing Sheets

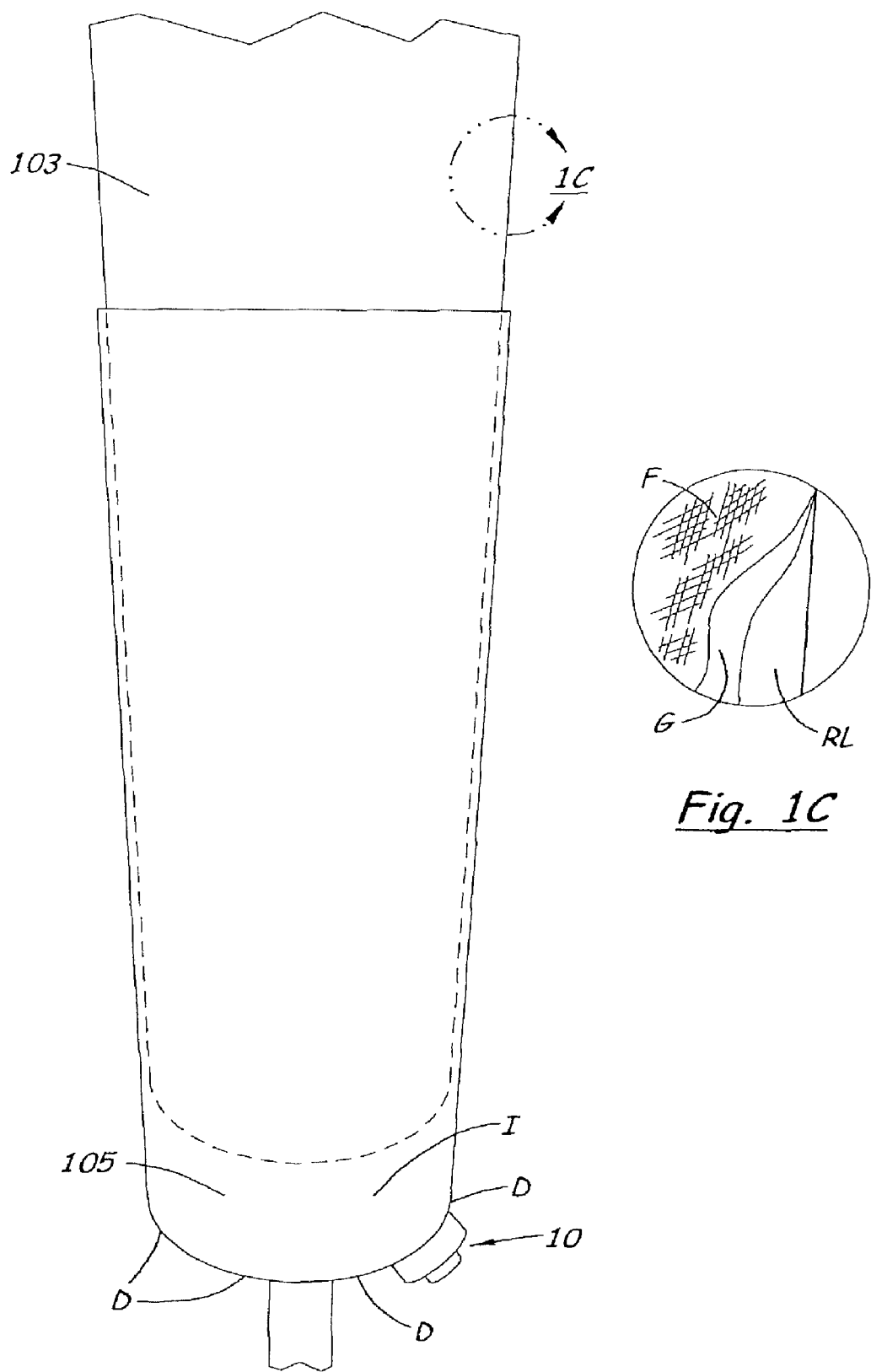

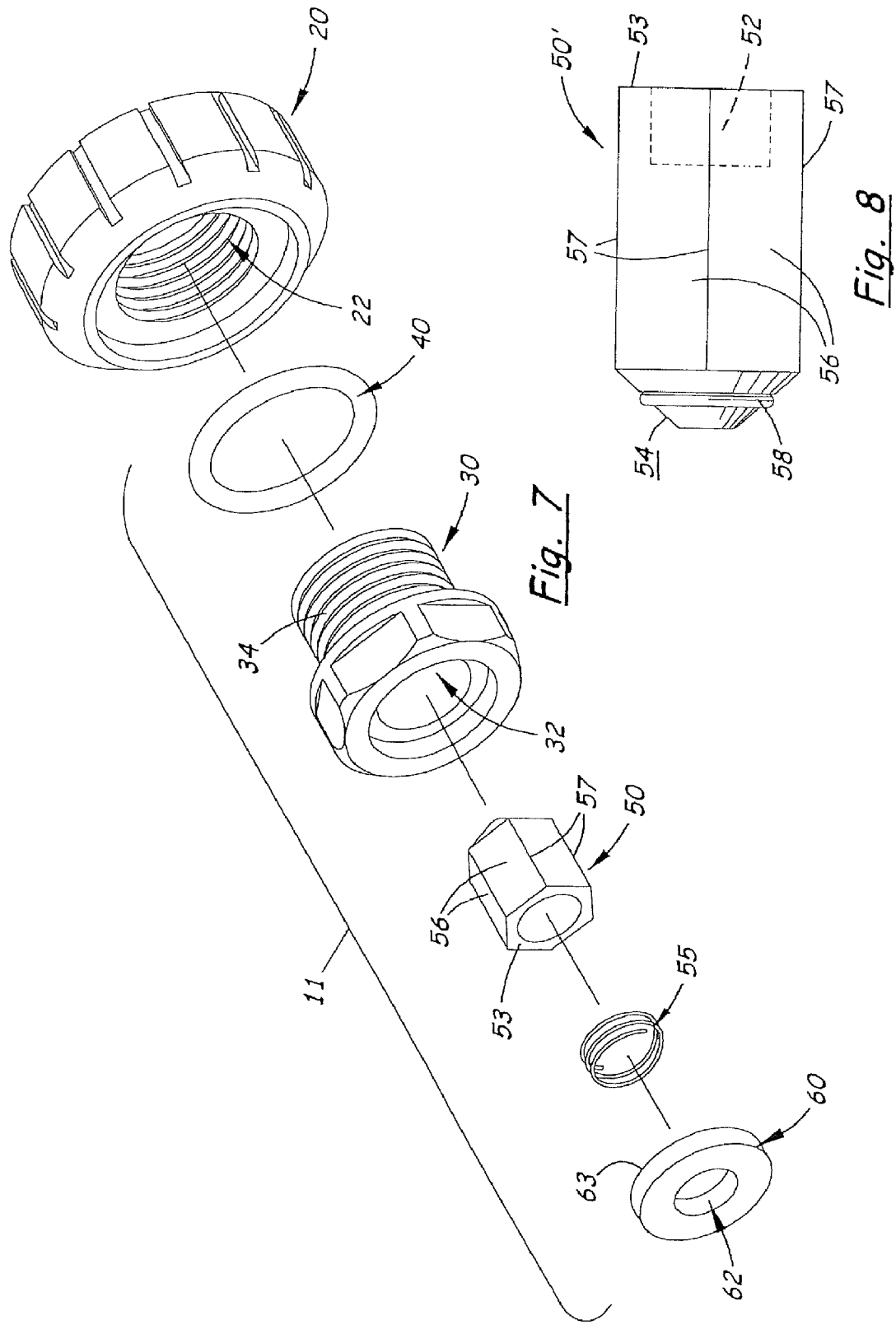

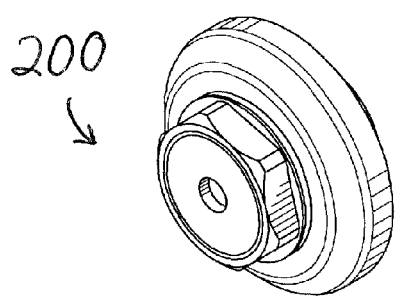
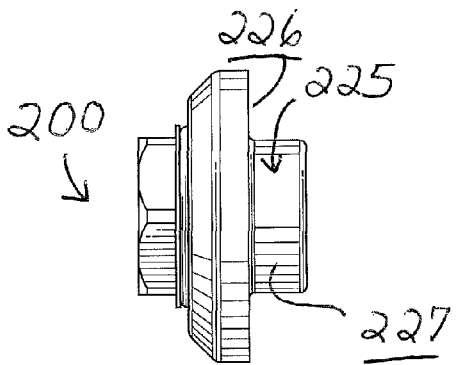
Fig. 9          Fig. 10
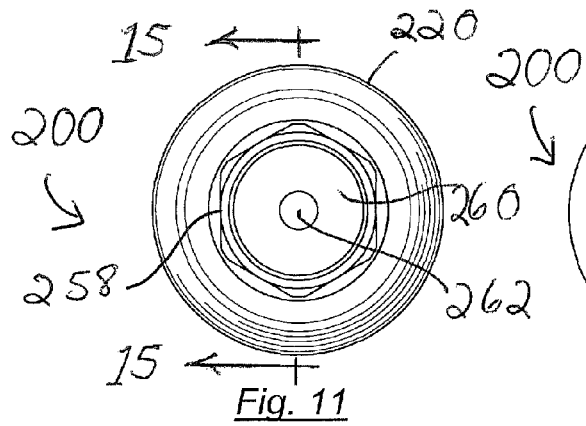
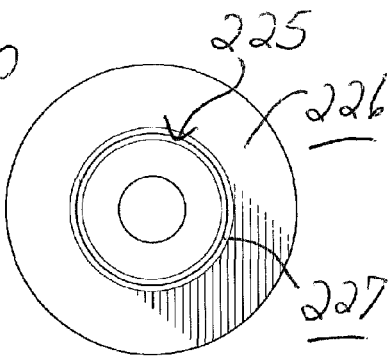
Fig. 11         Fig. 12
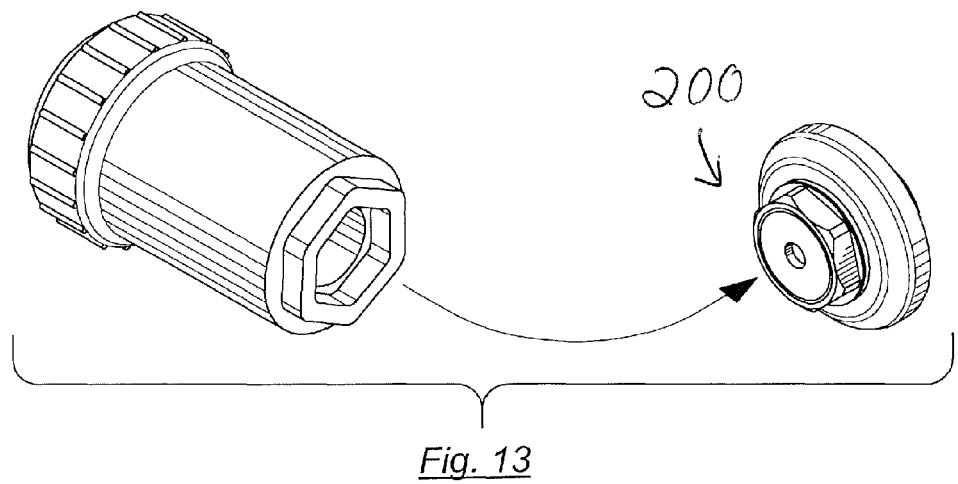
Fig. 13

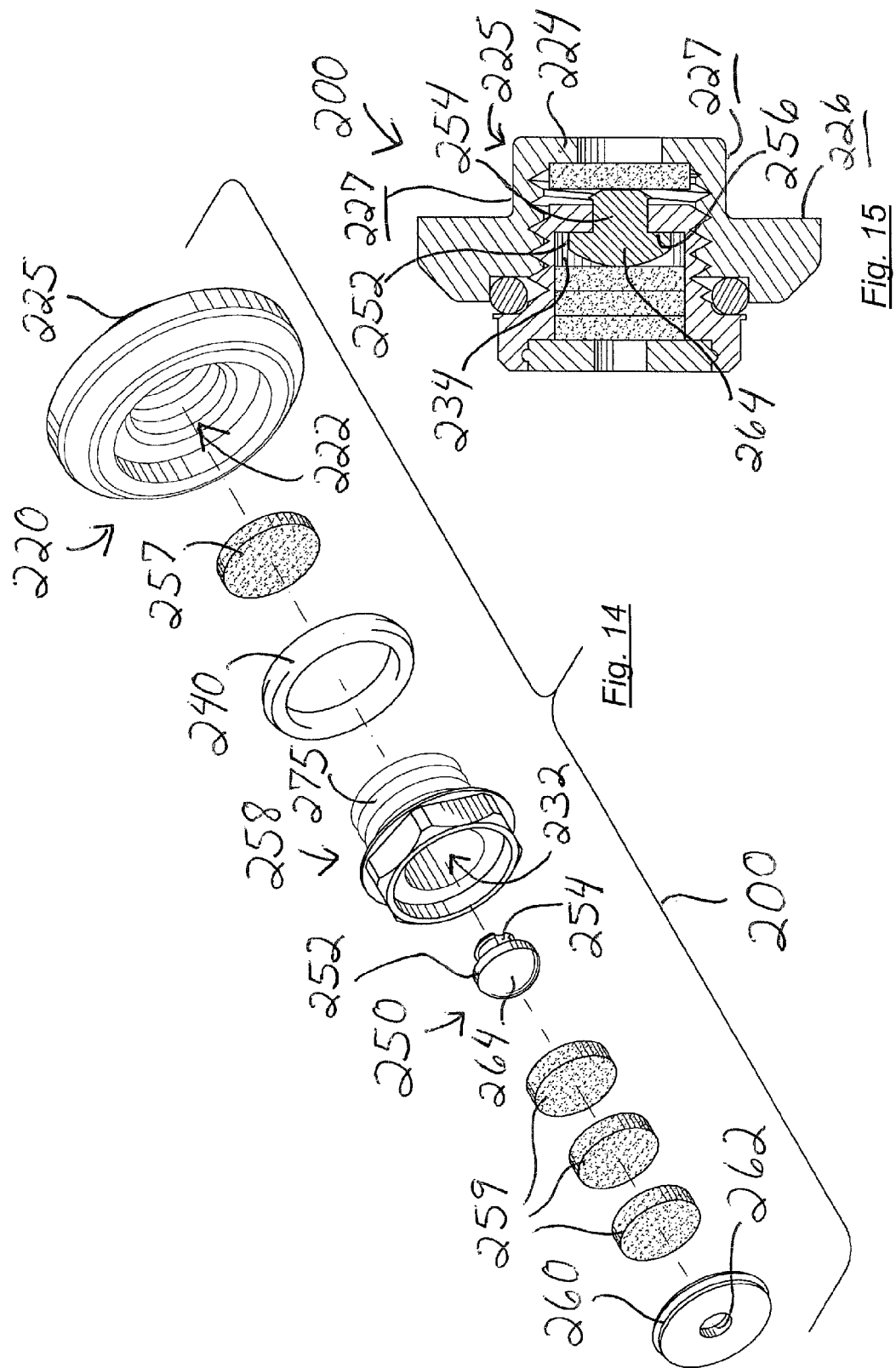

VALVE SYSTEM FOR PROSTHETICS

This application claims priority, and is a continuation-in-part, of Non-Provisional application Ser. No. 11/527,752, filed Sep. 25, 2006 now abandoned, which claims benefit of Provisional 60/719,785, filed Sep. 24, 2005.

BACKGROUND OF THE INVENTION

1. Field of the Invention

The present invention relates to an external prosthesis, and more specifically to a valve system for air release from a limb prosthesis.

2. Related Art

Gravitational and other forces tend to cause separation between a prosthetic limb and a residual limb. This happens, for example, during the swing phase of the gait, when a prosthetic leg is additionally subjected to centrifugal forces. The manner in which an artificial limb is suspended and/or attached to the residual limb determines the amount of control an amputee has over the prosthesis. Patients have routinely worn a variety of belts, straps, cuffs and harnesses to prevent the prosthetic limb from separating from the residual limb, but such devices are inconvenient and tend to cause chafing against the patient's body, giving rise to sores and abrasions.

It has long been appreciated that differential air pressure or "suction" may be utilized to retain or suspend, or assist in retaining or suspending, a prosthetic limb on a patient's residual limb. Suction suspension typically involves a hard socket and a cooperating liner positioned between the residual limb and the prosthetic socket. The liner is rolled onto the residual limb for a suction, slight compression, and/or gripping connection of the inner gel layer (or otherwise tacky layer) of the liner to the skin of the residual limb. The liner-covered limb is then inserted into the prosthetic socket, and the outer surface/layer of the liner preferably forms a suction, grip, or other interference fit to the socket to interfere with the socket falling off the limb.

These socket liners frequently have been called "suction liners," "gel liners," "roll-on liners" or "suspension liners" and include the "first generation" of gel-layer-only liners, and also the modern "second generation" of multiple-layer liners currently preferred by most wearers of prosthetics. These modern liners comprise a thin textile/fabric outer layer that is fixed to the gel-like inside layer. Thus, the second generation of liners is similar to the first in its connection to the residual limb, but its connection to the socket is modified by the presence of the textile/fabric layer. The term "suction liner" began with the first generation liners, which featured the gel layer contacting both the residual limb (liner's inner surface) and the socket (liner's outer surface), and which, therefore, could be used to create a fairly high amount of pressure differential between the inside of the socket (in the "well" of the socket) and the surrounding ambient air. The terms "suction liner" and "suction socket" are still used by many manufacturers, prosthetic technicians, insurance and medicare/medicaid entities, and wearers of prosthetics, even though the modern liners, with their textile/fabric outer layers, typically do not form what would be called "true" or "pure" suction with the socket, as further discussed below. See the discussion of suction liners in Janusson, et al. (U.S. Pat. No. 6,706,364) and Janusson, et al. (U.S. Pat. No. 6,626,952).

Socket liners are usually fabricated to be, or to include an inner layer of, silicone, urethane, or other gel-like material that grips the limb to such an extent that they need to be rolled-onto the limb from a rolled-up "doughnut" form, rather than pulled on like a sock. When rolled-on, there is little, if any, air remaining between the inner surface of the roll-on liner and the limb, and the roll-on liner is snug against the limb all the way around the circumference of the limb. Also, the inner surface of the roll-on liner is of such material and tacky texture that air will not be able to, or be very unlikely to, enter between the roll-on liner and limb. Thus, the roll-on liner may be said to form a suction fit and/or a slight compression fit with the limb. A distal force on the liner, such as caused by the swing of a gait with a prosthetic leg, may tug on the roll-on liner but typically does not loosen, lower, or remove the liner from the limb.

The hard socket is usually laminated or otherwise fabricated from polyethylene, polypropylene, or other copolymers, for example, and is donned over the liner and the residual limb. A suction-fit, including a partial-suction fit, as discussed above, may form between the liner-sheathed limb and the interior of the socket. A "true" suction fit (allowing high suction, greater amount of vacuum) will be more likely to form if 1) the liner exterior surface is smooth and flexible enough to conform to the contours of the residual limb, for example, non-air-permeable material such as the silicone, urethane, or other rubbery or gel-like material such as described above for the liner-to-limb connection; 2) if the interior surface of the socket is also smooth and non-air-permeable; and, of course, 3) if the socket has no un-sealed holes or apertures.

A "partial" suction fit (allowing lower suction, low amount of vacuum) is more likely to form if one of the above three conditions is not met, for example, if the outside of the liner is the thin fabric or other woven material bonded to a rubbery/gel-like interior layer of the liner, for example, as described above for "second generation" liners. In such a case, some air will tend to leak through or past the fabric layer of the modern liners into the well of the socket, that is, between the liner and the socket interior surface, so that there is typically not a true air-tight seal between the two. However, the air leaks fairly slowly because of the preferred close fit between the contour of the liner-cover limb and the contour of the internal surface of the socket. This slow air leakage and close fit typically allow their to be a "partial" suction fit between the socket and the liner outer surface, and this "partial" suction fit tends to be more comfortable for many wearers that a "true" or "full" suction fit. In other words, a textile/fabric-covered liner and the resulting "partial" suction tends to be more comfortable than the stronger "tugging" on the residual limb created by the "full" suction of first generation, gel-layer-only liner. The air that slowly leaks into space(s) in between the socket and the liner tends to be expelled with each step due to the force of the residual limb pushing into the socket. This way, modern, fabric-covered roll-on liners still tend to create some pressure differential between the well of the socket and the ambient air.

Therefore, many of skill in the field of prosthetics still apply the term "suction" to a fit or suspension of the prosthetic to the limb ranging from excellent suction (with a "true" seal, large resistance to equalization of pressure between the inside and the outside of the socket) to slight suction (with a "partial" seal, small resistance to said equalization such as in many popular liners). Therefore, the terms "suction," "suction-fit," and "suction suspension" herein are therefore not limiting to a particular amount of pressure differential, but to the general process known well in this field of providing a "roll-on" liner or other "interference" liner that helps keep a socket on a residual limb while creating at least a small amount of blockage/hindrance to air freely moving in and out of the socket well past the residual limb.

Therefore, it may be said that any region or amount of negative pressure in the space(s) between the liner-sheathed stump and the interior of the socket, relative to ambient (outside of the socket), may help to hold the prosthesis upon the limb during use. Certainly, more suction is more secure than slight suction, but there may be comfort sacrifices that result from more suction, for example, chaffing or pulling on the limb. A high-suction prosthesis suspension system may cause the user a discomforting disturbance of circulation in the limb on which the prosthesis is worn, due to the build up of a high amount of partial vacuum during walking, particularly in warm humid weather. Therefore, a very popular conventional roll-on liner is one such as the Ohio Willow Wood Alpha™ liner, which has multiple layers, that is, a rubbery/gel-like inner layer and a thin fabric outer layer bonded to the inner layer, so as to moderate the suction to a reasonably effective amount without allowing the great forces on the limb that can result from a high amount of suction. A "suction liner" or "roll-on liner" suspension, even in moderate range of suction provided by the preferred liners, gives the patient the ability to better control the prosthesis and provides for useful sensory or proprioceptive feedback. This is because there is a more intimate connection between the limb and the prosthetic, over much of the surface area of the limb, compared to old-fashioned waist belts, distal locks, or other methods. Suction or roll-on liner suspension also make a prosthesis feel lighter as compared to other forms of suspension.

A valve system may be used in combination with a suction/roll-on suspension system in order to regulate the air pressure in the socket, so that undesirable pressure differentials do not prevent or complicate the donning and doffing of the socket. Conventional valves aim at relieving buildup of pressure when the lined limb is inserted into the socket, which is typically a snug fit by design, to prevent a positive pressure inside the socket relative to outside of the socket (ambient air) and therefore to allow donning.

Because the typical valve system is a one-way valve, or "check valve," it is intended to maintain a slight negative pressure (slight, partial suction) relative to ambient once the socket has been fitted on the residual limb and used. The process of walking and other weight-bearing will tend to push the limb further into the socket, but the swing of the gait will tend to pull the socket off the limb. The pushing of the limb further into the socket may cause the valve to allow air to be expelled, and the pulling of the socket during the swing will tend to create suction in the socket because the valve will not allow air to enter through the valve.

In applications wherein the multi-layer roll-on liner allows air to slowly leak into the socket well, or wherein a seam, connection, lock or other aperture in the socket allows air to leak into the socket, weight-bearing steps will tend to expel air from inside the socket through the valve and then said leaking will tend to replace at least some of it (especially on the swing of the gait). Therefore, there may be frequent opening and closing of the valve, perhaps for each, or for many, of the user's steps. Many conventional valves for these applications are known to either not work very well, to plug easily, or to make embarrassing noise with each step.

There are many valve systems in use in the market. Typical valve systems use an inner base that resides inside of the socket and passes to the outside of the socket. The outer housing and the valve are then threaded onto the inner base or threaded to the socket wall in an attempt to create an air-tight seal. Such systems requires a generally flat socket wall surface for installing the valve and outer base to prevent air from leaking around the valve structure and out of the socket instead of being expelled through the valve at the desired air pressure.

Issued patents and patent publications relating to valve systems are listed as follows: Underwood (U.S. Pat. No. 1,586,015), Catranis (U.S. Pat. No. 2,530,285), Sharp et al. (U.S. Pat. No. 2,533,404), Hauser (U.S. Pat. No. 2,790,180), Edwards (U.S. Pat. No. 4,010,052), Carrow (U.S. Pat. No. 4,106,745), Greene (U.S. Pat. No. 5,201,774), Hill (U.S. Pat. No. 5,490,537), Hill (U.S. Pat. No. 5,709,017), Slemker et al. (U.S. Pat. No. 6,287,345), Perkins (U.S. Pat. No. 6,334,876), Hoerner (U.S. Pat. No. 6,361,568), Caspers (U.S. Pat. No. 6,508,842), Laghi (U.S. Pat. No. 6,544,292), Caspers (U.S. Pat. No. 6,761,742), Abrogast et al. (U.S. Pat. No. 6,797,008), Caspers (U.S. Publication No. 2004/0181290), and Patterson et al. (U.S. Publication No. 2004/0260403).

SUMMARY OF THE INVENTION

The present invention is a valve system for helping to regulate the air pressure in the space(s) between a residual limb, or liner-covered limb, and a hard socket of a prosthetic limb. The preferred valve is an externally-mounted "one-way" or "check" valve, with a valve stem that "pops" or otherwise opens consistently and quietly at a small differential pressure, for example, a pressure inside the socket (in the space(s) between said socket and the limb or liner-covered limb) that is $\leq 3$ psi pressure above ambient pressure (outside the socket). The valve may be adhesively mounted on the outside of the socket, and is easier to mount than conventional valves due to this preferred adhesive mounting and due to preferably no part of the valve being installed from the inside of the socket. The preferred valve has no threaded attachment to the socket, and, while some embodiments may have a base that extends into the wall of the hard socket, they preferably have no portion that extends into the well of the hard socket. The valve stem may have a polygonal side wall, or have other recesses or grooves in its side wall(s) to create passages through which air may flow quietly. Alternatively, the valve stem may be cylindrical and the channel in which the valve stem slides (the valve housing bore) may be polygonal or have recesses or grooves in its wall(s), to create passage through which air may flow quietly. Or, both valve stem and the housing bore may be non-cylindrical. Or, the valve stem may be an umbrella check valve member, or another one-way valve member having at least one flexible portion that flexes to move out of the way for one-way air flow past said at least one portion.

The low profile of the valve, and the quieter action of, and quieter air flow from, the valve may result in a less intrusive and less noticeable apparatus that is more acceptable and less embarrassing to wearers.

The valve system includes a base having an opening for receiving a valve assembly. The base may be installed on or near the outside surface of the hard socket, preferably without threaded connection between the base and the socket. A hole may be drilled in the hard socket from the outside surface of the socket to the inside surface of the socket, to align the hole in the socket with the bores/passages in the valve system. A valve housing holding the valve operating mechanism is then received in the opening in the base.

BRIEF DESCRIPTION OF THE DRAWINGS

FIG. 1B is a schematic view of a hard socket holding a residual limb with second generation roll-on liner, with one embodiment of the invented valve system installed on the hard socket distal portion. This view illustrates more accurately the preferred relationship of residual limb, roll-on liner, socket and valve.

FIG. 1C is a schematic cross-section detail view of a two-layer liner on a residual limb RL, such as in FIG. 1B, wherein the liner has an inner gal-layer G and an outer fabric layer F.

FIG. 7 is an exploded perspective view of the valve embodiment shown in FIGS. 1-6.

FIG. 8 is an alternative embodiment of a valve stem that has an o-ring in its end surface.

FIG. 9 is a side perspective view of another alternative embodiment of the invented valve.

FIG. 10 is a side view of the valve of FIG. 9.

FIG. 11 is a front view of the valve of FIGS. 9 and 10.

FIG. 12 is rear view of the valve of FIGS. 9-11.

FIG. 13 is a perspective view of a preferred wrench specially adapted to engage the polygonal front end of the valve housing of the valve of FIGS. 9-12, for aiding in disassembly of the valve of FIGS. 9-12, for example, to separate the internals from the base of the valve for cleaning or replacement of parts.

FIG. 14 is an exploded view of the valve of FIGS. 9-13.

FIG. 15 is a cross-sectional view of the valve of FIGS. 9-14, viewed along the line 15-15 in FIG. 11.

DESCRIPTION OF THE PREFERRED EMBODIMENTS

In the Figures, there are shown several, but not the only, embodiments of the preferred valve system for prosthetics.

As will be understood by one of skill in the art after reading this application and viewing the drawings, once the air pressure inside the hard socket (relative to the ambient pressure outside the socket) exceeds the "crack pressure" of the valve, the invented "check" valve or "one-way" valve opens and air is expelled out through the valve. This is useful during donning of the socket, as the insertion of the limb, or liner-covered limb, increases pressure in the socket well; the valve system opens to generally equalize the ambient pressure and the pressure inside the socket in order to allow the donning.

After donning, when the wearer takes each step, pressure is exerted downward on the limb, that is, toward the bottom of the socket well, and this also increases the pressure inside the socket well. Again, the preferred valve will "crack" or "pop" to relieve this pressure, and then close when the pressure is generally equalized by cessation of the downward pressure of the step, and/or when the swing phase of the gait suspends the prosthetic from the residual limb/liner and a slight suction/vacuum tends to be created in the socket. The preferred valve is designed with a "crack pressure" in the range of 3 psi differential, and more preferably 1-3 psi, or most preferably 1-2 psi, differential, so that, with this slight suction/vacuum, and preferably with any pressure differential below the "setpoint" (selected from the range of 1-3, or 1-2, psi positive pressure inside the socket well), the valve will close to not allow air into the socket through the valve.

Figure 1:
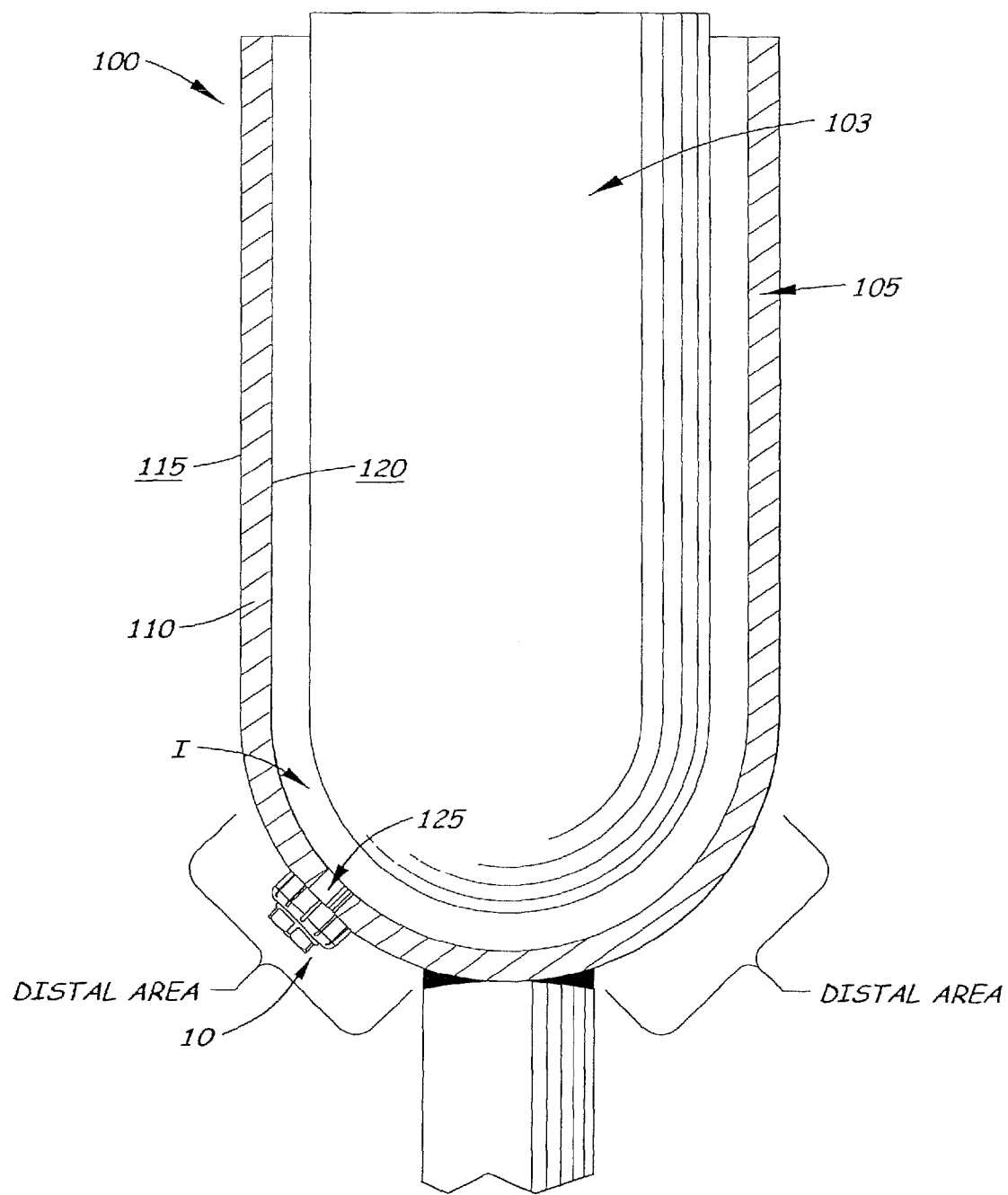
FIG. 1 is a schematic view of a hard socket and liner combination, wherein one embodiment of the invented valve is shown attached to the outside of the hard socket. In this view, the liner is shown as spaced from the socket, but it will be understood from the foregoing discussion, that the liner and socket will tend to be in close contact for at least part of the length along the socket and preferably all around the circumference of the liner and socket at or near the top of the socket. Some space between the liner-covered limb and the socket interior surface is normally present, so that the limb does not reach all the way to the distal end of the well of the socket.
Figure 2:
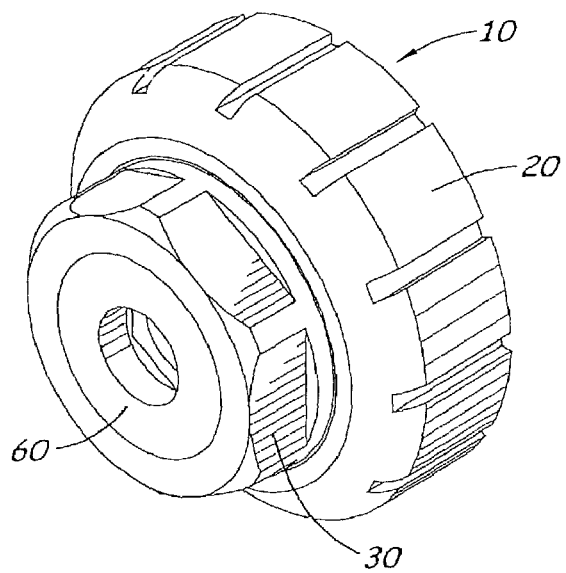
FIG. 2 is a front perspective view of the valve embodiment of FIG. 1, wherein the valve is one, but not the only, embodiment of the invention.
Figure 3:
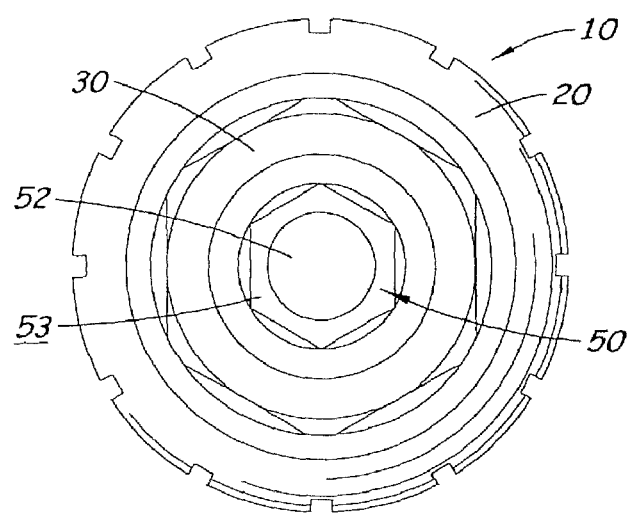
FIG. 3 is a front view of the valve embodiment shown in FIGS. 1 and 2, with a front o-ring/gasket removed to better show internals of the valve.

Referring to FIGS. 1-7, the valve system 10 is adapted to cooperate with a suspension system 100 for prosthetics, which, as discussed in the Related Art section, includes a liner that provides at least some blockage/hindrance to air passing between the socket and the liner. As shown in FIG. 1, the suspension system 100 comprises a liner 103 received on a residual limb, and a hard socket 105 adapted to fit over the liner 103 and residual limb. The hard socket 105 comprises a sidewall 110 defining an interior space I, wherein the sidewall 110 comprises an outer surface 115 and an inner surface 120.

The liner 103 is preferably a roll-on liner, and may be of various types, as discussed in the Related Art section, which provide varying amounts of "suction." Modern liners comprising both an inner gel layer and a textile/fabric outer layer are preferred, and the preferred valve system of the invention cooperates well with these liners; the valve system is specially adapted to allow air to be expelled quietly and consistently, even as often as every step, as may be desired with the amounts of air "leakage" experienced with fabric-covered liners.

As shown in FIGS. 2-7, the valve system 10 comprises a base 20 having an internally threaded circular bore 22 extending through the base 20. The base 20 is generally cylindrical in shape and is preferably fabricated from a durable polymeric material or "plastic." Alternatively, the base 20 may not comprise threads, but may instead have other adaptation for joining to the valve assembly that is inserted and secured to the base. For example, a bayonet or other latching mechanism that anchors or secures the valve assembly into the base may be used.

Figure 4:
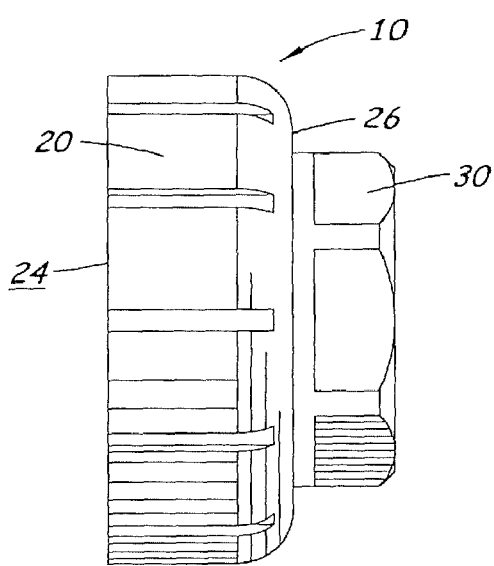
FIG. 4 is a side view of the valve embodiment shown in FIGS. 1-3.
Figure 5:
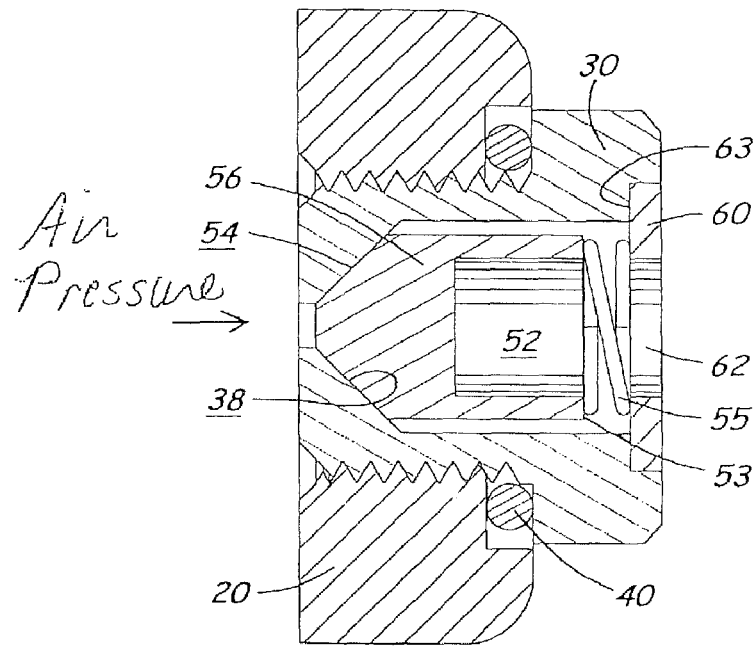
FIG. 5 is a cross-sectional side view of the embodiment shown in FIGS. 1-4, wherein the valve is shown in the closed position.
Figure 6:
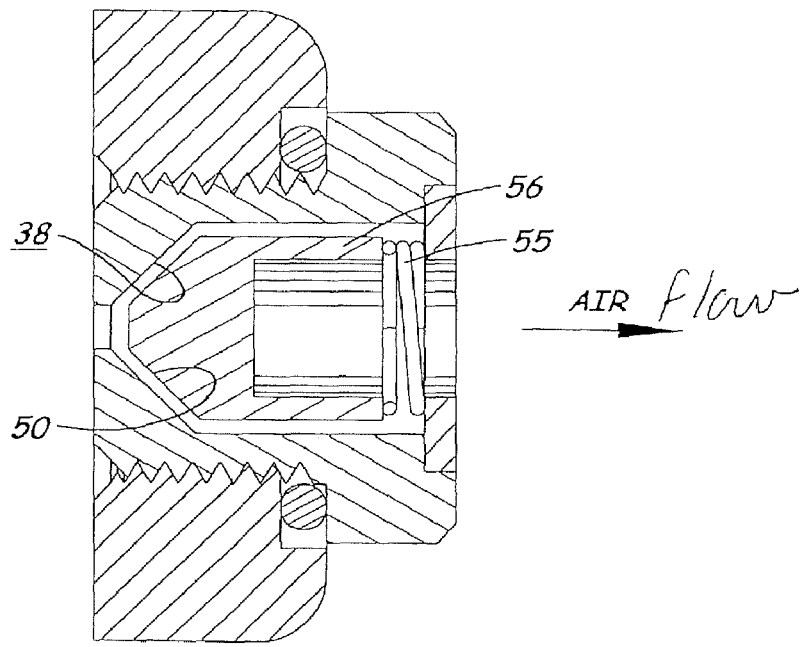
FIG. 6 is a cross-sectional side view of the embodiment shown in FIGS. 1-5, wherein the valve is shown in the open position.

The base 20 has a generally flat bottom portion 24 and a slightly curved or rounded top portion 26 (see FIG. 4). The bottom 24 of the base 20 may be slightly concave to mimic the contour of the outer surface 115 of the socket in the preferred distal installation area D on the socket (see Distal Area D on FIG. 1). This allows the valve system 10 to be placed on the distal portion/area D of the hard socket 105 so that it is discreet when covered by clothing and so it does not protrude (as it would from a more proximal side of the socket) to catch on clothing or other items.

After the base 20 is attached to the hard socket 105, preferably by adhesive, a hole 125 is drilled through the sidewall 110 of the hard socket 105 via the bore 22 in the base 20, so that the hole 125 generally aligns with the interior bore 22, and bore 32 and opening 62 discussed below, for fluid communication between the socket well, hole 125, bores 22, 32 and opening 62 to vent air out of the socket interior I.

One may see from the drawings that the preferred valve 10 has base 20, o-ring 40, valve housing 30, stem 50 and ring 60 all being coaxial, creating a passageway or "exit path" for air to pass through when the valve opens. In use, when the air pressure inside the hard socket 105 (between the liner-covered residual limb and the socket interior surface) exceeds the desired air pressure, as further discussed below, the air will force the valve stem 50 to move away from the opening 125 in the hard socket 105, compressing the spring 55 against the ring 60. This movement of the stem 50 unseats the end 54 of the stein from the sealing surface 38, allowing air to flow around the end 54 and along the sides of the stein to the opening 60 of the ring, and out to the ambient air.

The valve system 10 comprises the valve assembly 11 that is inserted into the base 20, which valve assembly 11 comprises a valve housing 30 having an internal circular bore 32 with a conical sealing surface 38 and an external threaded portion 34. The threaded portion 34 on the valve housing 30 has a slightly smaller diameter than the threaded bore 22 in the base 20, so that it may cooperate with the threaded bore 22 in the base 20. As explained above for the base 20, the valve housing 30 may be otherwise adapted for connecting/securing to the base. For example, the valve housing may not have any threads and may instead have bayonets that are received in slots in the base when the valve housing is inserted into and rotated in the base.

The exterior of the valve housing 30 is shown as "hex-shaped," but other shapes may be used, such as a other polygonal shapes or such as a cylindrical shape. The hex-shape is desirable as it may allow the technician to easily install and tighten the valve housing or the entire assembly in the base. Also, because the hex-shape provides a good surface to grip, it may allow the user to manually open the valve, in effect by disassembling the valve (removing the valve assembly from the base), if necessary, prior to the user removing his/her residual limb from the hard socket 105.

An o-ring 40 or other seal is placed in a recess in the base 20 between the base 20 and the valve housing 30. Once the valve housing 30 is threadably or otherwise received and secured in the base 20, an air tight seal is created between the base 20 and the housing 30.

The valve assembly 11 further comprises a valve stem 50 received in the bore 32 of the housing 30. The valve stem 50 slides axially inside the bore 32 to seat against the sealing surface 38 of the housing, when the valve is closed, and to move away from and unseat from the sealing surface 38 when the valve is open. A spring 55 biases the valve stem 50 into the closed, seated position to close the valve except when a differential air pressure overcomes the spring 55 bias and pushes the valve stem 50 away from the sealing surface. Spring 55 is preferably a cylindrical coil compression spring, the design of which is the main determining factor in the crack pressure of the valve.

The valve assembly, including the bias spring 55, are adapted so that a differential pressure selected from the range of 1-3 psi, and more preferably the range of 1-2 psi, will "crack" or "pop" open the valve. In other words, the valve assembly and particularly the spring 55 are preferably designed so that, when the pressure on the "inner side" of the valve (to the left in FIGS. 5 and 6, and typically on the inside of the socket between the liner-covered limb and the interior surface of the socket) is a certain amount above the pressure on the "outer side" of the valve (to the right in FIGS. 5 and 6, and typically outside the socket), then the valve will open. This "certain amount" is preferably in the range of 1-3 psi, and more preferably in the range of 1-2 psi. As soon as the differential pressure drops (that is, as soon as the inner pressure is less than the preferred 1-3 psi or 1-2 psi higher than the outer pressure) the spring 55 will again bias the valve stem 50 to the closed, seated position. Thus, as discussed above, the valve will open, if necessary, with each step, to allow air to vent from the socket well, and then quickly close after the air has been vented and/or when the swing portion of the gait lowers the pressure inside the socket well.

The valve stem 50 preferably has an internal bore 52 (or other hollow or recessed end or cavity that opens to the housing bore preferably at the spring-end of the valve) that may receive air that is flowing out of the valve in the "exit path" comprising passing around the stem, through or around the spring, and out through the outer end of the valve (at ring 60). Internal bore 52 may provide extra space for this flowing air, as it passes around or through the spring to exit the valve, thus helping prevent unpleasant noise or venting sounds that might occur with too-narrow portions of the exit path. Further, various embodiments of the bore 52 may be advantageous during the molding or machining process, for weight reduction, and/or for cooperating with or connecting to a spring or other bias member. The preferred location of the spring 55 is that is received between the flat face 53 of the valve stem 50 and the inner face 63 of the ring 60, and held there securely enough that it may be repeatedly compressed between those surfaces and then released, when the valve opens and closes, respectively, without significantly shifting from its preferred radially-centered position.

Further, as shown in FIG. 8, there may be an o-ring 58 or other material on the generally conical end 54 of the stem 50, which o-ring 58 or other material is preferably a softer or more flexible material, compared to the preferred brass valve stem 50, for enhancing the seal between the stem 50 and the sealing surface 38. Alternatively, the entire stem 50, the conical end 54 of the stem, or another portion of the stein may be made of a softer plastic or other material with enhanced sealing performance.

Retaining ring 60 is a generally thin disc that is friction-fit or otherwise secured and anchored into the bore 32 of the housing 30 to retain the spring 55 and the stem 50 in their proper positions inside the housing. The ring 60 is preferably secured to the housing, on ledge 39, in such a way that it will not normally come out of the housing, but that a prosthetics technician could pry or otherwise remove it to clean the valve assembly 11 and/or replace parts of the valve assembly 11. Ring 60 has an opening 62 through which the air is expelled. Alternative ways of retaining the valve stem, spring, and/or other parts as may be desired, in the housings of the valve may be used.

Stem 50 is a hexagonal, or other polygonal shape, so that it has multiple flat or generally flat sides 56. Therefore, the air may flow along the end 54 of the stem and through the bore 32 of the housing in between the housing inner surface and one or more of the flat sides 56. This provides multiple passages for the air, with each preferably being a relatively wide passage (that is, radially wider than if the stem where cylindrical inside a cylindrical housing bore), which is believed to be important for reducing air-venting noise. These passages may be said to be "spaced gaps" between the stem and the housing, in that they are spaced apart (separated) by the edges 57 of the stem, which contact, or come very close to, contacting the bore 32 surface. These gaps, therefore, may also be called non-annular gaps or non-annular spaces, as the gap/space between the stem and the bore of the housing is preferably not simply a continuous, annular space around the entire stern, but rather multiple axial passageways that are separated/spaced apart by the edges 57 that are close to, or that contact, the bore 32. It may also be said that, because the stem and the housing bore are not the same shape (and particularly not the same circumferential shape), there are multiple gaps between the stem and the housing bore created by this difference in shape. This also places the stem 50 in the housing in a slidable arrangement, where it slides axially in the housing bore 32, with contact being between the edges 57 of the sides 56 and the bore 32 surface, but not all the way around the circumference of the stem. This may be important for keeping the stem freely slidable in the bore 32 and less prone to plugging, seizing-up, and/becoming fouled to an extent that the valve would make more noise.

The axially-sliding stem, and a polygonal or other stem shape, that provides multiple air passages along the sides of the stem (which are relatively wide by being flat, recessed, or otherwise spaced from the preferably cylindrical housing bore wall) are believed to be one set of features that result in quiet, consistent, and effective operation of the valve. Also, the preferred low crack pressure that is achievable with the preferred valve with repeated, consistent operation, is believed to be important and beneficial for quiet operation and effective prosthetic suspension without large swings in socket pressure.

Preferably, the base 20, valve housing 30, and retaining ring 60 are fabricated from a light-weight durable material, for example, Delrin™ plastic; however, other materials may be used such as aluminum, titanium, nylon or other plastics. Additionally, the stem 50 may be brass, but also may be manufactured from other materials, for example, including other metals, plastics, or combinations thereof.

Valve system 10 is adapted to be fitted on the outside surface 115 of the hard socket 105, and most preferably only to the outside surface 115. The valve system 10 is preferably attached with adhesive, by applying adhesive of types known in the field of prosthetic sockets to the bottom 24 of the base and/or to the outer surface 115. Other securement means may be used, but adhesive is preferred as it has been found to be reliable, easy to use, and not requiring any other fasteners or complex or protruding parts. Preferably, no portion of the valve system 10 extends through the socket wall, or into the interior space I of the hard socket 105, or contacts the inside surface 120 of the hard socket 105. The opening/hole 125 in the socket wall is made by drilling or otherwise cutting through the socket wall, and this step preferably does not include any threading or other shaping or preparing of the socket or the hole therein. Thus, the preferred valve and attachment of the valve may be used effectively with modern thin-walled, light-weight sockets. The valve system 10, in the preferred but not all embodiments, consists essentially only of, and may consist only of, a base, a valve housing, an o-ring or other seal, a stem with or without supplemental sealing member or portion, a spring and a retainer ring or other closure or cover. This simple design is effective in terms of manufacture, installation, and operation, and has many benefits over prior art valves, including over the prior art valves that are more complicated, prone to plug-up, prone to make venting noise, that include ball-and-spring systems, and/or that screws/threads into the socket wall and/or that resides on both sides of the socket wall. In the preferred embodiment of the invented valve system, only the base, and more preferably only its bottom surface (24) or portions of the bottom surface (24), is in contact with the hard socket, and preferably only in contact with the outer surface of the socket or the generally cylindrical wall of the bore/hole through the socket wall. Preferably no portion of the valve extends into the well of the hard socket and no portion of the valve is in contact with the inner surface of the socket.

FIGS. 9-15 illustrate an alternative, especially-preferred embodiment of the invented valve, which provides especially-quiet and especially-reliable air expulsion for donning, doffing, and daily use of the hard socket and leg prosthetic. This valve 200 uses a valve member that comprises no spring and no bias system other than its own flexibility and resilience. At least a portion of the valve member flexes upon the pressure inside the socket well reaching the "crack pressure", which is preferably in the range of 3 psi differential, and more preferably 1-3 psi, or most preferably 1-2 psi, differential. Thus, with a suction/vacuum, and preferably with any pressure up to the "set-point" crack pressure, the valve will remain closed and not allow air into or out of the socket through the valve. Upon reaching the crack pressure, the valve will open to expel air out from the socket well W (also referred to as socket interior I earlier in this document).

The preferred valve member is an umbrella valve 250, which features a circumferential lip 252 extending around a stein 254 so that the valve member is substantially symmetrical around its central axis. Elastomeric umbrella valves are commercially available from multiple manufacturers, and may be selected without undue experimentation to provide the desired "crack pressure" for valve 200. The lip 252 is of such a flexibility (by virtue of its elastomeric characteristics) that it will move/flex away from a cooperating sealing surface 256 of housing 258, when the pressure inside the distal region of the socket well reaches the crack pressure. This moving/flexing away from the sealing surface 256 allows air to enter the valve 200 by flowing through the dampening pad 257, around the valve member 250, and through the filter pad(s) 259 to exit the valve 200 at the cover ring 260 opening 262. Also, the elastomeric characteristics of the stem 254 of the valve allow the valve stem 254 to be installed into the housing by being snapped into a cooperating aperture provided in the rear end 275 of the housing, wherein the valve stem 254 is retained in said cooperating aperture but does not block the entire aperture. This way, the valve stem 254 remains in place in the aperture when the valve lip 252 is seated or opened.

Alternative elastomeric one-way valves may be used, for example, those with other relative dimensions compared to the umbrella valve shown, for example, a flatter, less mounded flexing portion. The inventors have found, however, that the illustrated umbrella valve exhibits a very accurate and reproducible response at the desired low crack pressures, and, when the accurate, low-crack-pressure valve member is combined with the preferred at least one sound-dampening pad and at least one filtration-pad, the resulting valve gives repeated, consistent, and quiet performance. This performance helps prevent uncomfortable and/or high-noise-producing swings in the pressure inside the socket well.

Dampening pad 257 is provided in a space inside the bore 222 of base 220 between a rearward inwardly-protruding flange 224, of the rear protrusion 225 of the base, and the stem 254 of the umbrella valve 250. Dampening pad 257 mainly serves the purpose of dampening sound that may be caused by the expelling of air through the valve, while it may also protect the valve 250 from dust and dirt if any enters the well of the socket.

Filter pads 259, provided in the bore 232 of the housing 258, mainly prevent dirt from reaching (and fouling or otherwise interfering with) the valve member 250, but may also perform some sound-dampening. Multiple pads 259 may be replaced with fewer or more pads, for example, a single thicker pad may serve the filtering (and optional dampening) purposes while filling the space provided in the housing bore 232. Said space extends from the surface of the umbrella head at the head central axis to the inner surface of the ring 260, and reaches to the wall surface of the bore 232.

Preferably, the pad(s) 257, 259 are made of one or more fabrics, such as a felt, various woven materials, or open-cell foam that has/have air filtering and sound-deadening capability. Preferably, pad(s) 259 fill the space between the umbrella valve head and the ring, and may be thinner or fewer in number if a relatively larger umbrella valve head is used.

One may note that, while the pad(s) 259 fill the entire diameter of the bore 232 of the housing 258, to prevent bypassing of air around the outer circumferential perimeter of the pad(s), the head 264 of the umbrella valve 250 does not reach to the cylindrical wall of the bore 232. This way, as soon as the lip 252 flexes/moves away from the sealing surface 256, air will flow around the lip 252, through the space 234 between the lip 252 and the bore 232 wall, and then through the pad(s) 259 to exit at opening 262.

Figure 16:
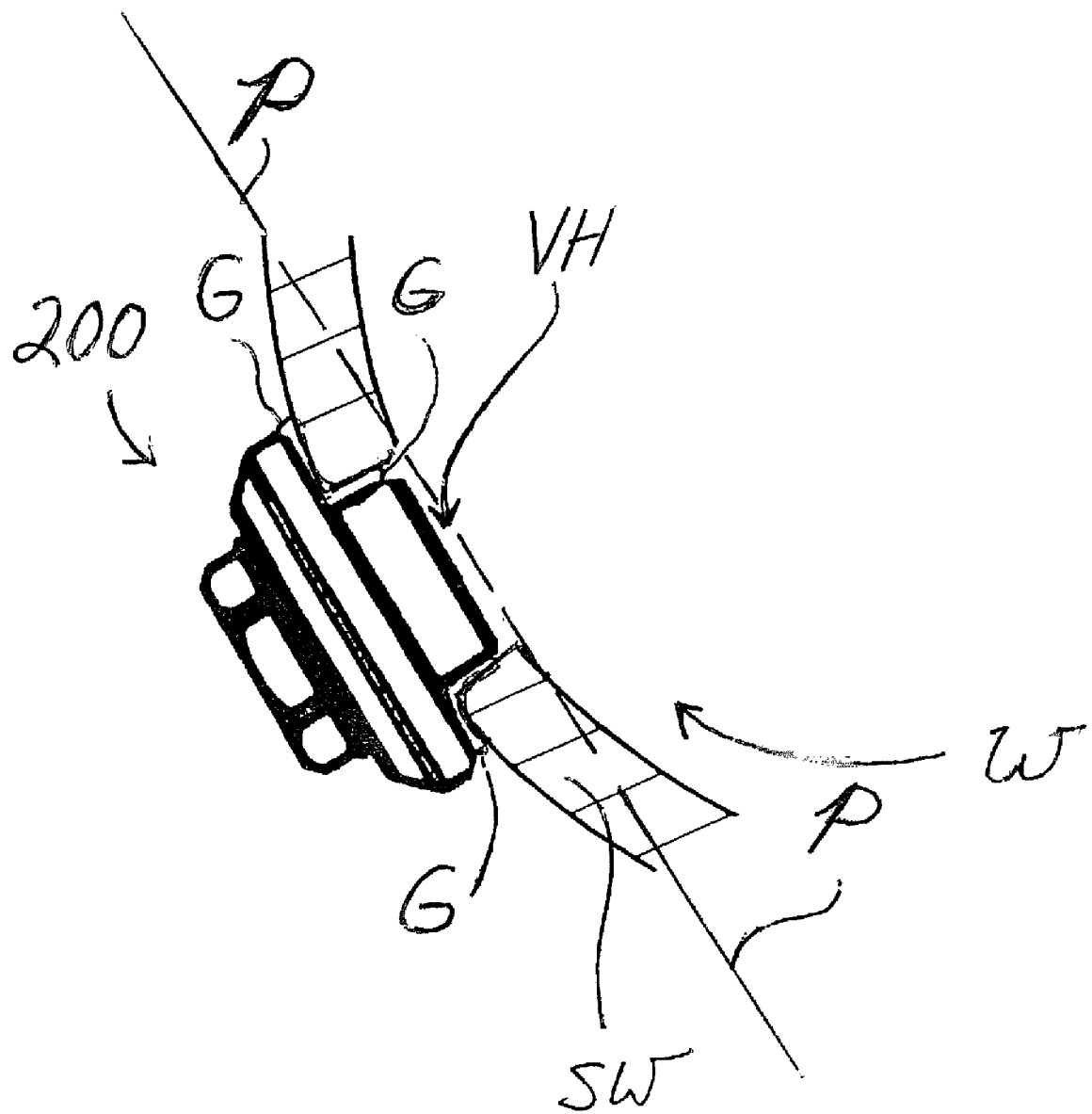
FIG. 16 is a schematic, enlarged view of a distal region of a hard socket, and with the valve of FIGS. 9-15 shown installed according to one method of the invention.

Base 220 includes a rear protrusion 225, of which flange 224 is a part. This rear protrusion 225 extends into a hole formed in the socket, in order to help stabilize the valve relative to the socket wall and to receive a portion of the valve internals to reduce the amount the valve protrudes out beyond the outer surface of the socket. As may be seen in FIG. 15 to best advantage, some of the internals or portions of the internals, specifically part of the valve 250 and the dampening pad 257, reside in the interior space of the rear protrusion 225. The rear protrusion 225 preferably extends to, or nearly to, the plane P of the inside surface of the socket wall, as shown in FIG. 16. However, the protrusion 225 preferably does not protrude farther, specifically, not inward past the plane P, that is, not into the well W of the socket. Thus, the axial length of the protrusion 225 is the same or less than the thickness of the wall SW of the socket in the region in which the valve is being installed.

The valve 200 does not require and preferably does not include any structure inside the well, wherein the well is defined as the interior space of the socket but not including the valve-receiving hole VH. Thus, as described above for other embodiments, valve 200 does not require that the person who installs the valve (whether it is the manufacturer of the socket, or a prosthesis technician, for example) install any structure inside the well, from inside the well, or into the hole VH from a direction originating inside the well.

Valve 200 may be installed much the same as other embodiments described herein, except that a hole VH is created in the wall of the socket that may be larger than in the case of valve 10. The hole VH for valve 200 should be approximately the size of the outer diameter of the protrusion 225, so that the valve may be inserted or pressed into the hole VH from outside of the socket. Adhesive or glue G is preferably used to seal surface 226 to the outer surface of the socket, and to seal the outer cylindrical surface 227 of protrusion 225 to the wall of the hole VH, thus securing the valve 200 on the socket and preventing air from bypassing the valve by flowing between the socket wall and the valve 200. See FIGS. 10 and 16 to see the glued surfaces and preferred location of adhesive/glue G to best advantage. Less preferably, separate sealing gaskets may be used in addition to adhesive, but it is preferred that a threaded connection between the valve and the socket is not used. The lack of a threaded connection is particularly beneficial in installations of the valve 200 in modern, thin-walled hard sockets.

One may see from FIGS. 9-16 that the components of valve 200 are preferably coaxial around a central axis of the valve 200. The preferably cylindrical housing rear end 275 screws into the base 222, with an o-ring 240 or other seal providing an air-tight seal between the housing and the base. Said o-ring 240 or other seal prevents air from flowing between the housing and the base, and the air must instead flow between the valve 250 and the housing 258 if it is to escape from the socket through the valve. Preferably, circular/cylindrical ring 260 snaps tightly into the front end of the housing, but need not necessarily seal perfectly to the housing. This is because air will more easily flow out of the opening 262 than in-between the ring 260 and housing 258, and also because a perfect seal between the ring 260 and the housing 258 is not imperative for proper operation of the valve 200.

Preferred embodiments of the invented valve may be described as a pressure-control system for a prosthetic hard socket, wherein the prosthetic socket comprises a wall having an outer surface and an interior surface defining a well for receiving a residual limb, and said wall has a hole extending from said outer surface to said interior surface; and wherein the valve system comprises: a base connected to said outer surface and having a base bore positioned over said hole in the wall; and the valve housing being connected to said base and extending into said base bore and having a housing bore generally coaxially aligned with said base bore and in fluid communication with said hole in the socket wall, said valve housing having a sealing surface; a valve stem, or valve member, received in said housing bore and slidable, or flexible, respectively, into a first, sealed position wherein a portion of said valve stem/member seals against said sealing surface and into a second, unsealed position away from the sealing surface. A spring biasing the valve stem, or elastomericity (or flexibility and resilience) of the valve member, causes the stem/member to remain in the first, sealed position until said air pressure inside the prosthetic socket well is at a differential pressure in the range of 1-3 psi greater than ambient pressure outside the socket, at which time the valve stem/member is pushed by said differential pressure into said second, unsealed position so that air leaves the socket well by flowing through the hole and through the valve system. In the case of an elastomeric valve member, a spring or other bias member (other than the elastomeric property of the valve member) is not needed. The valve stem/member circumference preferably is not the same shape and/or not the same size as the housing bore circumference, so that, when the valve stem/member is in the second, unsealed position, air more easily flows around the valve stem/member through circumferential gap(s) between the valve stem/member and the housing bore wall. Preferably, this difference in circumference/shape occurs along the stem/member side portion, which is a portion not adapted to contact the sealing surface. The venting of air sooner (at lower differential compared to the ambient air pressure) and with less-restricted flow, compared to prior art vents, and with preferably at least one noise-dampening pad in the air-flow-path, are features believed to be instrumental in reducing or eliminating the sudden, louder pop, squeak, or sputtering sounds of prior art devices.

The invention may also comprise the methods of installing and using such a valve system. For example, some embodiments of the invention may comprise a method of installing a pressure-relief valve in a prosthetic socket, the method comprising: providing a hard socket; providing a one-way air valve comprising a base with a base bore, a removable valve stem/member housing with a housing bore, and a spring for use with a valve member that is not itself biased by virtue of elastomericity. The base of the valve is adhesively attached to the outside of the socket and, in some embodiments, to the generally cylindrical wall of a hole in the socket wall.

The installation may include drilling a hole through the socket by inserting a drill bit through said base bore and drilling through the socket to make a hole in the wall generally coaxially aligned with said bore in the base. Alternatively, the installation may include forming/drilling a hole through the socket wall prior to adhesively attaching any part of the valve and then aligning and adhesively attaching the valve base to the socket and inside the hole.

The valve stem and spring, or the elastomeric valve member, and preferably at least one filter or dampening pad forward of the valve member, and a front-end retaining ring, are assembled into the housing by insertion into the housing bore. In the case of an elastomeric valve member, the valve member may be snapped into a receiving aperture in the housing. At least one noise dampening pad and/or filter pad is preferably provided in the base, so that it is provided between the housing and along the air-flow-path upstream of the valve member. The housing with its internals are then threadably connected to the base, to be generally coaxially aligned with said base bore and said hole in the wall. After installation and assembly of the valve on the socket, the valve is used for venting of air out of the socket well when pressure builds in the socket to a differential pressure that is greater than ambient pressure.

Preferably, the method comprises no insertion of any part of the valve into the socket well, and no part of the air valve extends through the socket wall so far that is protrudes into the well. Preferably, the only attachment of the valve to the socket is adhesive connection of the base to the outer surface of the socket, and optionally to the generally cylindrical surface of the hole formed/drilled through the socket wall, and, preferably, there is no threaded attachment of the air valve to the socket.

Although this invention has been described above with reference to particular means, materials and embodiments, it is to be understood that the invention is not limited to these disclosed particulars, but extends instead to all equivalents within the broad scope of the following claims.

The invention claimed is:

1. A pressure-control system for a prosthetic hard socket, the pressure-control system comprising:
   a prosthetic socket comprising a wall having an outer surface and an interior surface defining a well for receiving a residual limb, and said wall having a hole extending from said outer surface to said interior surface and having a generally cylindrical hole wall;
   a valve system comprising:
      a base connected to said outer surface and to said hole wall, and having a base bore positioned over said hole in the wall;
      a valve housing removably connected to said base by a threaded connection and extending into said base bore and having a housing bore generally coaxially aligned with said base bore and in fluid communication with said hole in the socket wall, the housing bore having a front portion, and a rear portion nearer the prosthetic socket, wherein said rear portion has a smaller diameter than said front portion, the housing having a rearward radial flange having a radial rear surface and a radial front sealing surface and an aperture through the radial flange that is said rear portion of said housing bore; and
      an elastomeric umbrella valve member having a head and a stem, the stem end being retained in said aperture by snapping into said aperture, and the head being received in said front portion of the housing bore, the head comprising an elastomeric outer perimeter that rests in a first, sealed position against said front sealing surface and that resiliently flexes into a second, unsealed position away from the front sealing surface when the air pressure inside the prosthetic socket well is at a differential pressure in the range of 1-3 psi greater than ambient pressure outside the socket, at which time the elastomeric outer perimeter is pushed by said differential pressure into said second, unsealed position so that air leaves the socket well by flowing through the hole and through the valve system by flowing past the stem through the aperture and through the front portion of the housing bore and out a front end of the housing;
   wherein the valve system further comprising at least one sound-dampening and filtering pad behind the elastomeric umbrella valve member and extending across the bore of said base between the housing and the base, and at least one sound-dampening and filtering pad in front of the elastomeric umbrella valve member and extending across the housing bore in the front portion of the housing bore, wherein the housing further comprises a retaining ring connected to the front end of the housing adapted to retain said at least one pad in front of the elastomeric umbrella valve member inside said front portion of the housing bore, wherein the retaining ring has an opening for air flow exiting the housing; and
   wherein the valve system comprises no spring.

* * * * *